United States Defensive Publication [19] (H) [11] T967,005

Wade et al. [43] Feb. 7, 1978

[54] CELLULOSE REAGENTS INCORPORATING T-AMINO GROUPS

[75] Inventors: Clinton P. Wade, Jefferson; Stanley P. Rowland, New Orleans, both of La.

[73] Assignee: The United States of America as represented by the Secretary of Agriculture, Washington, D.C.

[21] Appl. No.: 768,809

[22] Filed: Feb. 15, 1977

Related U.S. Application Data

[62] Division of Ser. No. 625,722, Oct. 24, 1975, Pat. No. 4,017,259.

[51] Int. Cl.[2] ..... C07D 251/08; C07C 125/06

[52] U.S. Cl. ..... 544/220; 560/160

[57] ABSTRACT

Durable press properties are imparted to cellulosic fabrics by reacting with either of two new tertiary amino-N-methylol reagents. Autocatalysis was shown by these reagents when applied as the free bases or as hydrochlorides to cotton fabric by conventional methods. Resilience, recurability, improved scorch resistance, and enhanced dye and brightener sorptions are realized.

6 Claims, No Sheets Drawing,

28 Pages Specification

The file of this unexamined application may be inspected and copies thereof may be purchased (849 O.G. 1221, Apr. 9, 1968).